Figure 2:
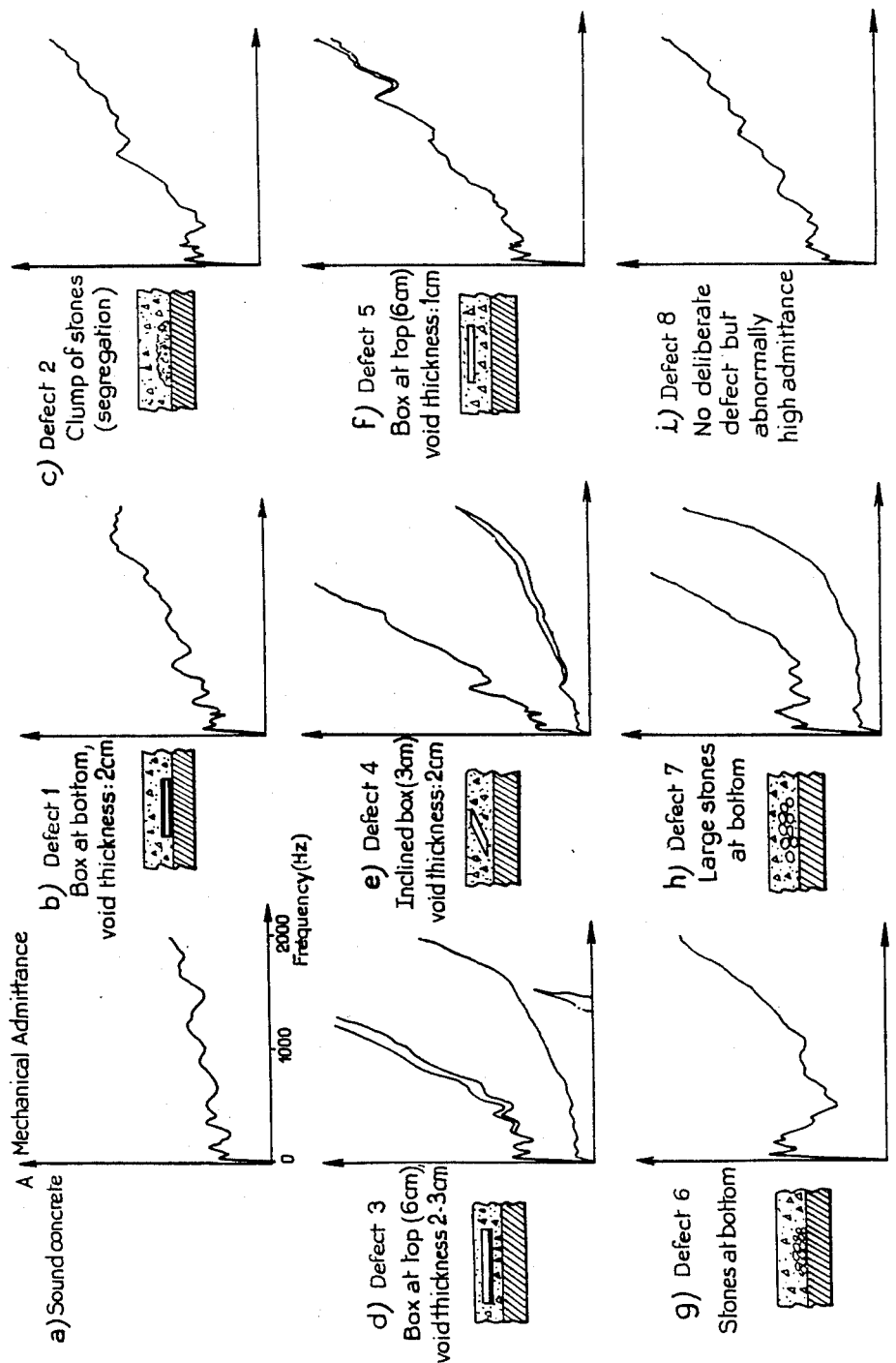

United States Patent [19]

Paquet

[11] Patent Number: 4,881,405

[45] Date of Patent: Nov. 21, 1989

[54] METHOD AND DEVICE FOR MECHANICAL TESTING OF CIVIL ENGINEERING STRUCTURE SURFACINGS

[75] Inventor: Jean Paquet, Plaisir, France

[73] Assignee: Centre Experimental De Recherche et D'Etudes Du Batiment, France

[21] Appl. No.: 145,147

[22] Filed: Jan. 19, 1988

[30] Foreign Application Priority Data

May 21, 1986 [FR] France .................................. 86 07234

[51] Int. Cl.[4] ............................................. G01M 19/00
[52] U.S. Cl. ...................................................... 73/146
[58] Field of Search ................... 73/146, 12, 579, 584, 73/649, 78, 81, 82, 84, 104

[56] References Cited

U.S. PATENT DOCUMENTS

| | | | |
|---|---|---|---|
| 3,481,183 | 12/1968 | Swift | 73/146 |
| 3,888,108 | 6/1975 | Brands | 73/12 |
| 3,937,065 | 2/1976 | Milberger | 73/649 |
| 4,163,393 | 8/1979 | Gutierrez et al. | 73/584 |
| 4,519,245 | 5/1985 | Evans | 73/579 |

FOREIGN PATENT DOCUMENTS

| | | | |
|---|---|---|---|
| 0648902 | 2/1979 | U.S.S.R. | 73/146 |
| 0121395 | 10/1984 | United Kingdom . | |

*Primary Examiner*—Donald O. Woodiel
*Attorney, Agent, or Firm*—Thomas J. Greer, Jr.

[57] ABSTRACT

The method comprises the determination of at least one signature ($2a$) of the response to an impulse shock of a sound reference coating or covering, and a plurality ($2b$–$2i$) of signatures of the response of an impulse shock to a covering having sample defects in order to establish reference signatures. The covering to be controlled is subjected at a plurality of test points (Pi) to at least one impulse shock test in order to determine the corresponding measurement signatures (MSi). A comparison of the measurement signatures with the reference signatures makes is possible to identify defects by resemblance criteria. Application to the control of coatings of traffic roads such as motorways for motor vehicles and runways for aircraft.

18 Claims, 6 Drawing Sheets

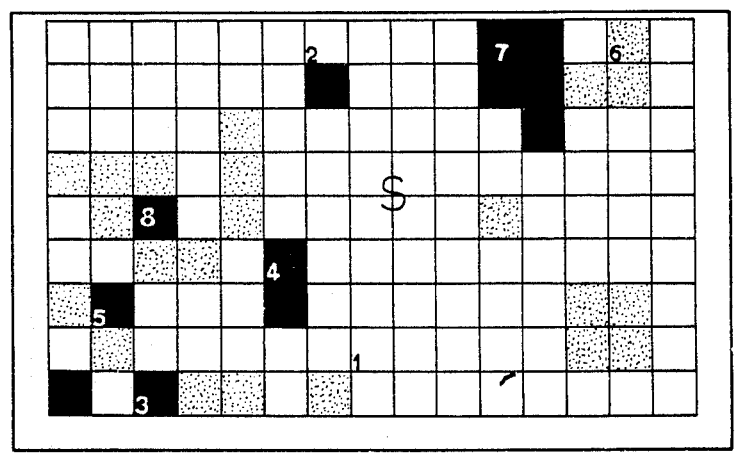
FIG_1
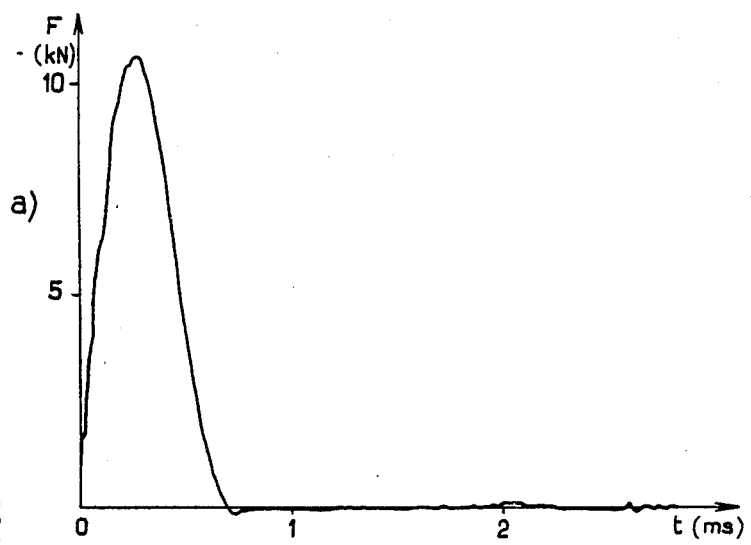
FIG_3

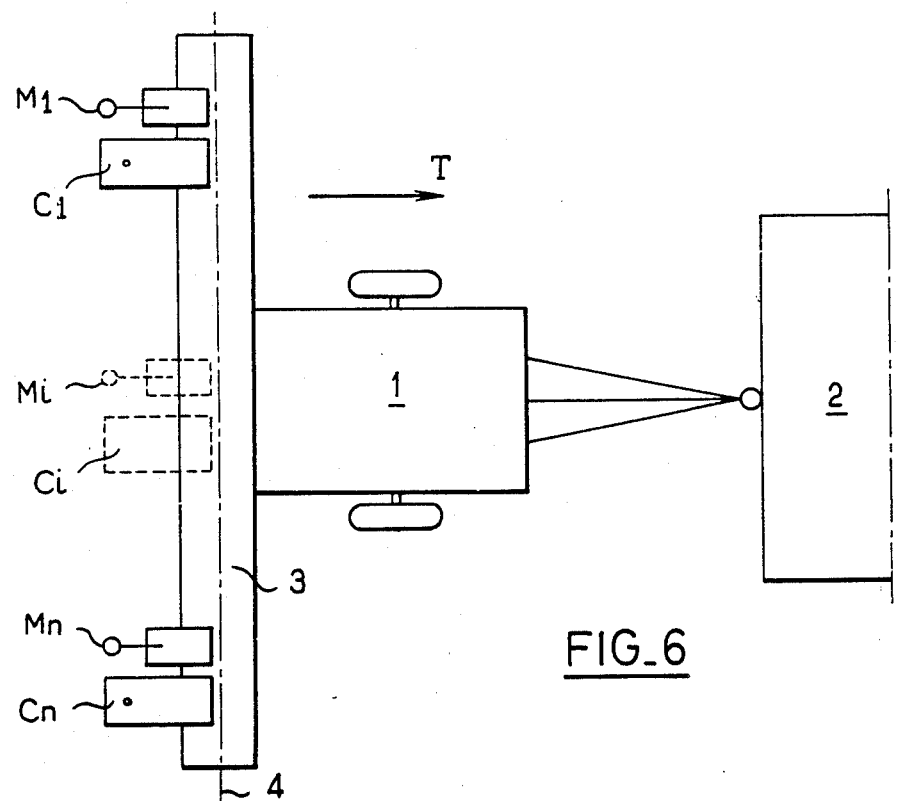
FIG_6
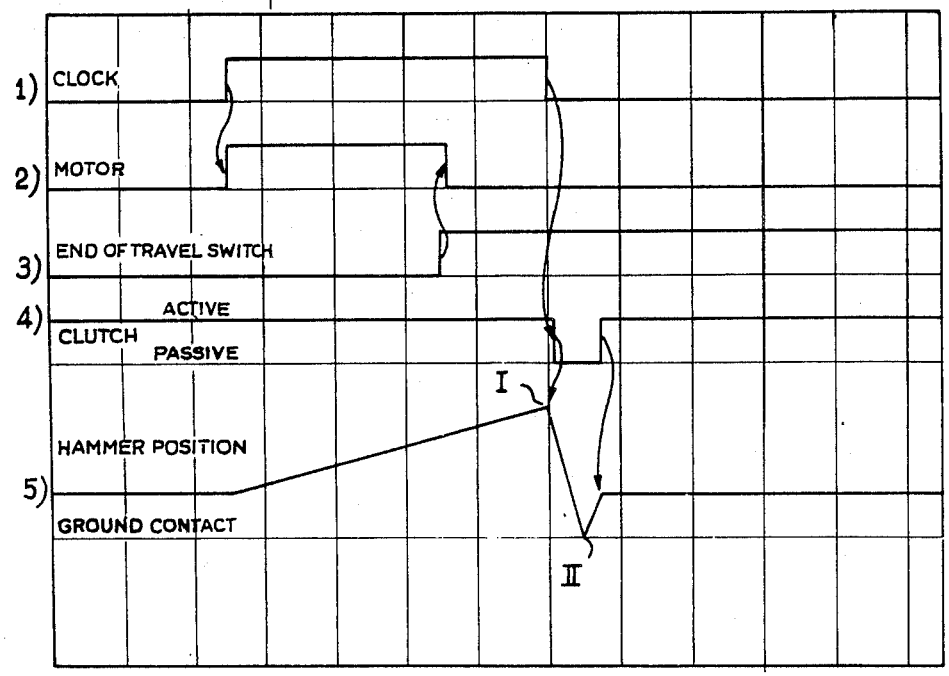
FIG_7c

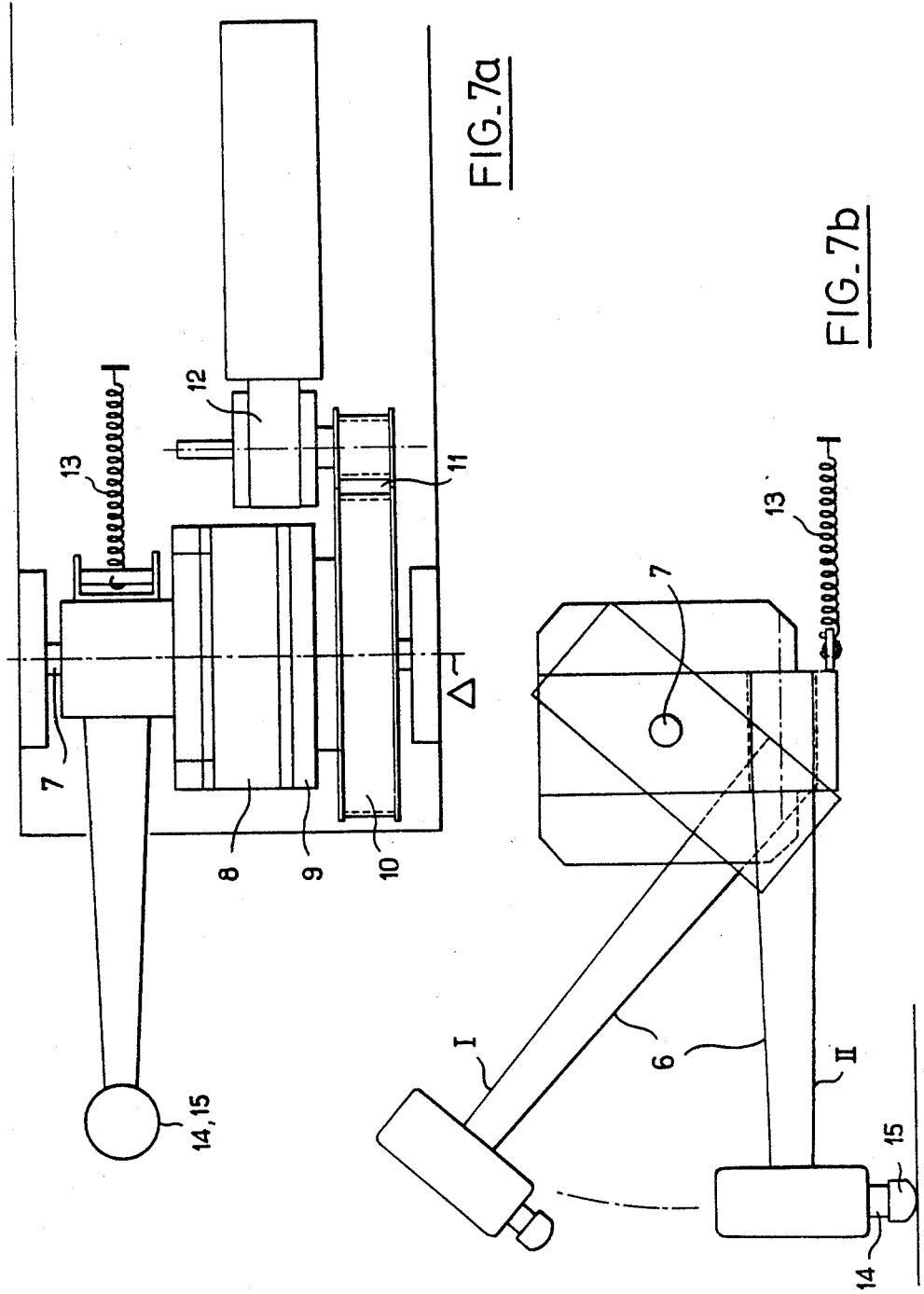

METHOD AND DEVICE FOR MECHANICAL TESTING OF CIVIL ENGINEERING STRUCTURE SURFACINGS

This application is a continuation of PCT International Application No. PCT/FR87/00177 filed May 21, 1987.

The present invention relates to a method and device for mechanical testing of civil engineering structure surfacings.

At present the mechanical testing of the surfacings of civil engineering structures such as paths, roads, motorways and runways for aircraft remains somewhat unsatisfactory. Such structures can have defects due to their construction or defects resulting from subsequent damage due to movement of the soil or subsoil, especially in the case of paths. In the particular case where the surfacings consist of concrete slabs cast in situ with or without a metal reinforcing grid the constructional defects previously mentioned can include clumps of aggregate and voids due to the reinforcing grid, for example. Subsequent damage results in particular from relative movement between the surfacing and the underlying layers of soil or subsoil; in the case of concrete slabs forming the surface surfacing of motorways, damage results in particular from the phenomenon of pounding of the slabs due to the circulation of vehicles, decompacting of the underlying soil resulting in the creation of voids. The testing methods proposed until now essentially comprise mechanical testing methods using vibrating rollers and electromagnetic methods using georadar.

The aforementioned mechanical testing methods consist in subjecting the surfacing to mechanical vibration at a fixed frequency and measuring the amplitude of the corresponding vibrations. The mechanical vibrations employed are produced by a roller vibrating at a frequency between 10 and 20 Hz.

Although the difficult problem of sensing the response of the surfacing has been solved in a satisfactory way through the use of a hydrophone wheel, there is no way that the aforementioned response can be regarded as providing comprehensive information on the mechanical state of the surfacing and of the interfaces between it and the soil, given the incomplete nature of the spectrum of frequencies generated by the vibrating roller.

Electromagnetic testing methods using high-frequency electromagnetic waves involve detecting reflections of the electromagnetic waves emitted from structural discontinuities in the surfacing or from its interfaces with the soil. However, given the nature of the waves transmitted, not all material discontinuities in the surfacing or in its interfaces will necessarily produce interference by reflection that can be measured in a reliable way, and interpreting the measurement results is extremely difficult. Also, and by virtue of the nature of the waves employed, the measurement results are highly sensitive to the moisture content of the surfacing and its interfaces and to the presence in the surfacing or in the underlying layers of metal materials.

One object of the method and device for mechanical testing of civil engineering structure surfacings in accordance with the invention is to remedy the aforementioned disadvantages, the inherent disadvantages of both the prior art methods in particular being eliminated.

Another object of the present invention is the provision of a method and a device for mechanical testing of civil engineering structure surfacings in which the surfacing is subjected to mechanical vibration in a wide frequency spectrum.

Another object of the present invention is to provide a method and a device for mechanical testing of civil engineering structure surfacings that can be implemented on a quasi-automatic basis.

Another object of the present invention is to provide a method and a device for mechanical testing of civil engineering structure surfacings in which the probability and reliability of detection are high.

The method in accordance with the invention for mechanical testing of civil engineering structure surfacings is remarkable in that it consists in establishing at least one signature of the response to an impulse impact of a reference sound surfacing and a plurality of signatures of the response to an impulse impact of a same type surfacing in which reference sample faults have been produced, the aforementioned signatures constituting reference signatures. A plurality of points on the surfacing under test are subjected to at least one impulse impact test so as to determine the so-called measurement signature of the impulse response at each of the specific points. The measurement signatures are compared with the refererence signatures to establish an identification based on criteria of resemblance.

The device in accordance with the invention for mechanical testing of civil engineering structure surfacings is remarkable in that it comprises a mobile support adapted to be moved over the surfacing. Percussion means disposed on this support make it possible to generate sequentially calibrated test impacts on the surface. Sensing means fastened to the mobile support but mechanically decoupled from it serve to deliver an electrical signal representative of the impulse response of the surfacing to the calibrated test impacts.

The method and the device in accordance with the invention are applicable to the mechanical testing of civil engineering structure surfacings of all kinds and in particular paths such as roads, motorways and runways for aircraft, for example.

Their object will be better understood from a reading of the following description and reference to the accompanying drawings in which:

FIG. 1 represents the topography whereby various sample defects are laid out over a reference test area, FIGS. 2a through 2i respectively show the nature of the surfacing, with or without a sample defect, and the corresponding reference signature constituted by the impulse response of the corresponding reference point in question.

Figure 4:
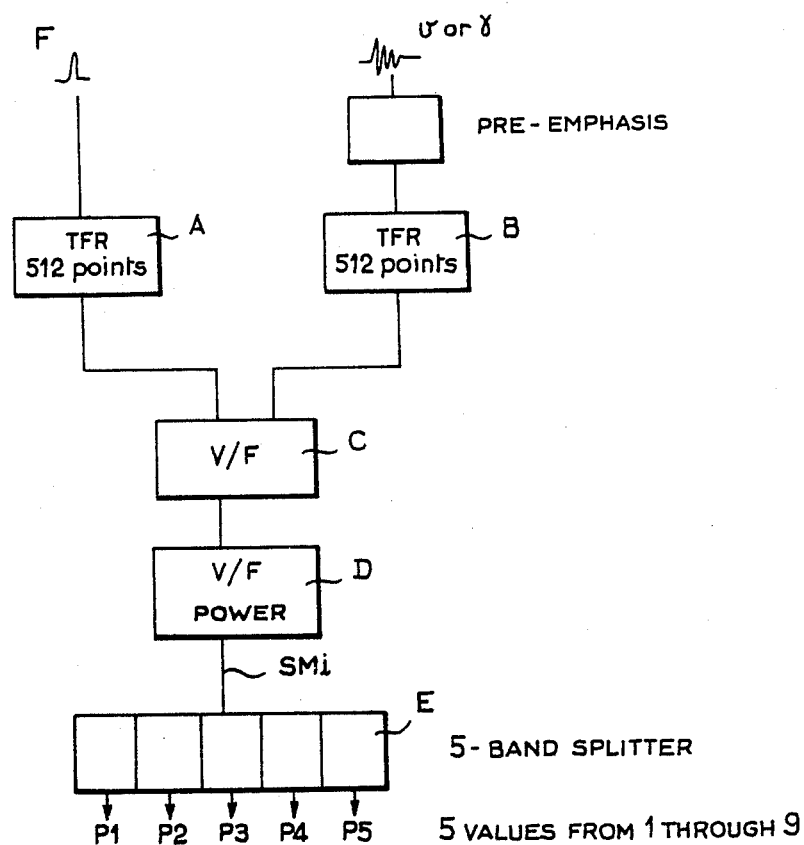
Figure 5:
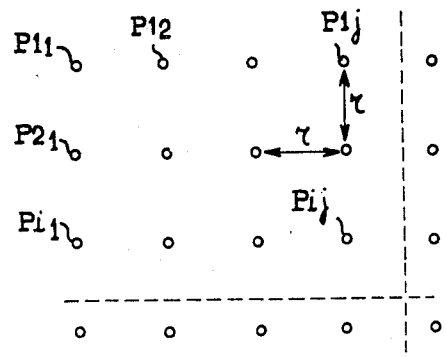

FIG. 3 shows amplitude-time and amplitude-frequency curves for a calibrated impact in accordance with the present invention, FIG. 4 shows a block diagram of a processor for applying the choice criteria of the method in accordance with the invention, FIG. 5 is a diagram illustrating the implementation of the method in accordance with the invention, FIG. 6 is a schematic plan view of a device in accordance with the invention, FIGS. 7a and 7b show a detail of the device as shown in FIG. 6 and FIG. 7c shows a timing diagram for various component parts from FIGS. 7a and 7b, FIGS. 8 and 9 respectively show a particularly advantageous embodiment of an essential part of the device and the device in accordance with the invention.

The method in accordance with the invention for mechanical testing of civil engineering structure surfacings will first be described with reference to FIGS. 1 and 2.

By civil engineering structures there is meant, of course, any structure in the civil engineering domain and in particular, but not in any limiting way, any surfacing of paths such as roads, motorways and runways for aircraft.

The method in accordance with the invention for mechanical testing of civil engineering structure surfacings consists in establishing at least one signature of the response of a reference sound surfacing to an impulse impact. A plurality of signatures of the response of a surfacing of a surfacing of the same type to an impulse impact is then established, for a surfacing in which reference sample defects have been formed. The signatures relating to the reference sound surfacings and to the surfacings comprising sample defects constitute reference signatures.

FIG. 1 shows a reference test area indicating the topography according to which the various sample defects have been laid out. The test area may thus correspond to a particular surface area and, in the particular case of motorway surfacings made up from concrete slabs of standardized dimensions, one of these slabs. A signature of the response to an impulse impact for a reference sound surfacing, the area denoted S in FIG. 1, is shown in FIG. 2a. In the same way there is established a plurality of signatures respectively shown in FIGS. 2b through 2i of the response of a surfacing of the same type in which various reference sample defects have been formed to an impulse impact. In FIG. 2b the defect corresponding to area 1 in FIG. 1 corresponds to a box situated at the bottom of the surfacing, that is to say above the foundation supporting the latter and corresponding to a void approximately 2 cm thick. Likewise, the sample defect introduced in the area 2 in FIG. 1 corresponds to a clump of aggregate caused by segregation of the latter, which separate out from the cement grouting constituting the concrete while the latter is being cast. The corresponding signature is shown in FIG. 2c. FIG. 2d shows the signature of a sample defect situated in area 3 of the reference area shown in FIG. 1, this sample defect consisting of a box disposed near the surface of the surfacing and corresponding to a void 2 to 3 cm thick. Note in this case the very strong increase in the offset of the signature, this increase actually necessitating a reduction of scale to enable it to be represented properly. Likewise, the sample defect introduced in area 4 of the reference test area shown in FIG. 1 corresponds to an inclined box with a void thickness of approximately 2 cm, the corresponding signature being shown in FIG. 2e. Once again, note the very high variation in the offset of the corresponding signature relative to a sound concrete surfacing as shown in FIG. 2a, for example. The sample defect in area 5 of the reference test area shown in FIG. 1 corresponds to a box disposed near the surface of the surfacing, this box corresponding to a void thickness of approximately 1 cm. The corresponding signature is shown in FIG. 2f. The signature shown in FIG. 2g corresponds to a clump of stones situated near the interface between the surfacing and the foundation. A change in the average offset of the corresponding signature will be noted in this figure. The sample defect corresponding to the signature of FIG. 2g is situated in area 6 of the reference area shown in FIG. 1. The sample defect in area 7 of this same reference area corresponds to a defect comparable with the sample defect in area 6, but in which the stones are larger. The signature corresponding to the sample defect of area 7 is shown in FIG. 2h. In this latter case there will again be noted a slight variation of the offset of the corresponding signature, followed by a significant increase in this same offset. Finally, the signature shown in FIG. 2i corresponds to a defect in area 8, where there is no deliberate sample defect, an abnormally high mechanical admittance appearing in the aforementioned area. The corresponding signature is shown in FIG. 2i and in this figure a substantially constant value of the average offset of the signature will be noted.

Using the method in accordance with the invention, the surfacing under test is subjected at a plurality of specific points thereon denoted Pi to at least one impulse impact test so as to determine the so-called measurement signature denoted SMi of the impulse response at each of the aforementioned points Pi. As seen in FIG. 2 in particular, but in a non-limiting way, the reference signatures shown at 2a through 2i and the measurement signatures SMi are responses to an impact pulse in a mobility-frequency diagram. The reader is reminded that the mobility at the test points Pi considered is the ratio of the speed at the measurement point to the force of the impact applied to it. Other parameters such as the acceleration at this point may of course be used, in a non-limiting way. Thus, as shown in FIGS. 2a through 2i, the mobility-frequency diagrams are graduated in frequency along the abscissa axis and in mechanical admittance along the ordinate axis, the mobility being assumed as representative of the mechanical admittance at the measurement point in question. Using the mechanical testing method in accordance with the invention, the impact pulses used to establish the reference and measurement signatures are calibrated impact pulses. To give a non-limiting example, as shown in FIG. 3, the calibrated impact pulses may advantageously consist in an impact pulse having a duration less than 1 ms and a peak amplitude greater than 100 daN, for example. The amplitude-time diagram for the corresponding calibrated impact pulse is shown in FIG. 3a, FIG. 3b showing the distribution of energy as a function of frequency for the calibrated pulses. The distribution of energy as a function of frequency for the calibrated impact pulses is such that the energy corresponding to a frequency in the order of 2 kHz is greater than one tenth of the maximal energy at low frequencies, for example.

In an advantageous embodiment of the method in accordance with the invention said measurement signatures are compared with the reference signatures, in a non-limiting way, by comparing specific values from the mobility-frequency diagram for the measurement signatures, denoted SMi, with corresponding values referred to as inherent values of the reference signatures previously shown in FIGS. 2a through 2i. The aforementioned identification may then be arrived at by calculating a coefficient of correlation or of resemblance between the reference signatures and the measurement signatures.

A particularly advantageous example of such calculation will now be described with reference to FIG. 4.

Referring to this figure, the signals representing the amplitude of the impact pulses denoted F and those representing the speed or acceleration at the test point Pi are sensed as a function of time beginning from the reference time, for example. These signals, after conversion into digital signals, for example, are then respectively submitted in steps A and B to fast Fourier transform processing for a specific number of points. In an advantageous embodiment of the method in accordance with the invention, the fast Fourier transform may be applied to 512 samples or values. In the case of the signal representing the speed or acceleration at the test point Pi in question, the signal is pre-emphasised by filtering it before it is subject to the fast Fourier transform processing. The values obtained are then subjected to the processing denoted C in FIG. 4 which makes it possible to establish for certain specific frequency bands the amplitude-phase relationship between the values obtained from the fast Fourier transform processing in the preceding steps A and B. The aforementioned amplitude-phase values in fact correspond to the ratio of complex values for the speed at the test point Pi in question to the corresponding impact amplitude for the frequency band in question. A second stage of processing may then be applied in the step marked B in FIG. 4 in such a way as to determine the corresponding energy in each frequency band considered. The results obtained in this way may be combined in a final step E which makes it possible, for example, to define energy values in the frequency bands considered related to a plurality of frequencies referred to as inherent values in the case of the reference signatures, for example. Of course, analogue processing is effected relative to the signals constituting the measurement signatures at each test point Pi. Correlation with a view to establishing the criteria of choice is then effected between the values corresponding to the inherent values of the reference signatures and of the measurement signatures. The mathematical method for processing the values as employed in the method in accordance with the invention will not be described in more detail, being specified by way of non-limiting example only.

According to one advantageous characteristic of the method in accordance with the invention, the previously determined points designated Pi at which the surfacing is subject to at least one impulse impact test may advantageously be distributed in a meshed array, the array increment being determined according to the resolution required. FIG. 5 shows a array of points of this kind, the points previously designated Pi being now designated with the general reference letters Pij, in such a way as to constitute the mesh of a array. In a non-limiting way, the array shown in FIG. 5 corresponds to a array in which the increment is exactly the same in two directions at right angles. Of course, the increment in these two dimensions or directions may be chosen differently, according to the required application. Measurements carried out using the method in accordance with the invention have made it possible, using a array with an increment r of 1 meter, to obtain a resolution of better than 30 cm. Of course, reducing the array increment makes it possible to increase the resolution required of the system. Establishing measurement signatures denoted SMij relative to each point Pij of the array then makes it possible to establish a true map of the surfacing and of the mechanical structure of the interfaces between the surfacing and the foundation supporting it.

A detailed description of a device in accordance with the invention for mechanical testing of civil engineering structure surfacings enabling implementation of the method in accordance with the invention as previously described will be given with reference to FIGS. 6 through 9.

Referring to FIG. 6, the device in accordance with the invention comprises a mobile support denoted 3 that can be moved in a direction denoted T in the aforementioned FIG. 6 over the surface of the surfacing to be tested. It will be noted, for example, that the mobile support 3 is fastened to a carriage denoted 1 provided with wheels, for example, which is itself towed by an automobile vehicle denoted 2 during implementation of the method. The support 3 may be rendered mobile relative to the surfacing by any means, of course, depending on the application of the method and the device in accordance with the invention. Percussion means denoted Mi are disposed on the support 3, these means making it possible to generate sequentially on said surface of the surfacing to be tested calibrated test impacts. Also, sensor means denoted Ci are fastened to the mobile support, these sensor means being mechanically decoupled from the support 3. By mechanical decoupling is meant any means of obtaining maximum attenuation of any mechanical vibration due to displacement of the support 3 relative to the surface of the surfacing for the aforementioned sensor means Ci. Thus, given the previously described mechanical decoupling, the sensor means Ci are able to deliver an electrical signal representative of the impulse response of the surfacing at the test point Pi considered to the calibrated test impact generated by the percussion means Mi.

As seen also in FIG. 6, the percussion means Ci are advantageously constituted by a plurality of percussion members aligned in a direction δ on the mobile support 3. The percussion members Mi and the sensor means Ci may advantageously be adjustable in relative position in the alignment direction.

As also seen in FIG. 6, with each percussion member Mi is associated a sensor member Ci, the set of sensor members constituting the previously described sensor means. In a non-limiting way, each group constituted by a percussion member Mi and a sensor member Ci may of course be adjustable in translation along the alignment direction δ. Thus installation of the percussion members Mi and their associated sensors Ci with a predetermined increment makes it possible for a particular dispacement of the mobile support 3 in the translation direction T to generate the array of test points Pij previously described in FIG. 5. As already mentioned, the array may be a square or rectangular array. According to one characteristic of the device in accordance with the invention for testing civil engineering structure surfacings, the distance separating a percussion member Mi from the corresponding sensor member Ci associated with it preferably does not exceed 10 cm.

A more detailed description of the percussion members Mi will now be given with reference to FIGS. 7a and 7b in particular.

Referring to FIG. 7a, which shows a plan view of a particular percussion member Mi, each of these members comprises a percussion head denoted 14, 15 mounted at the end of an arm denoted 6 forming a lever arm. The arm 6 forming a lever arm is rotatable about a shaft denoted 7 in FIGS. 7a and 7b, substantially parallel to the alignment direction. Drive means 8, 9, 10 for the arm 6 make it possible through the intermediary of the percussion head 14, 15 to generate a plurality of successive calibrated impacts as previously defined.

The calibrated impacts may, as previously mentioned, consist in an impact pulse with an amplitude between 100 and 1000 daN and a duration less than or equal to 1 ms.

As seen also in FIGS. 7a and 7b, the electromechanical clutch coupling device denoted 8, 9 is mechanically fastened to the arm 6 forming the lever arm. The electromagnetic clutch coupling device may be a device available through normal trade channels, for example, in particular an electromagnetic clutch coupling device distributed by the company BINDER MAGNETIC. Drive means denoted 10, 11, 12 serve to rotate said clutch, the drive means consisting of a motor-gearbox unit, for example. The rotational drive means 11, 12 and the clutch coupling device 8, 9 serve to displace the arm forming the lever arm 6 and the percussion head 14, 15 into a calibrated impact armed position. This calibrated impact armed position of the percussion head 14, 15 and of the arm 6 is denoted I in FIG. 7b.

As will be noted also in FIGS. 7a and 7b, return spring means 13 mechanically fastened to the support 3 for example and to the arm forming the lever arm 6 are also provided. The return spring means 13 and the clutch coupling device 8, 9 make it possible to displace the arm forming the lever arm 6 and the percussion head 14, 15 into the calibrated impact position. In FIG. 7b in particular the calibrated impact position is denoted II.

A timing diagram for the functioning of the various component parts of each percussion member Mi shown in FIGS. 7a and 7b will be given with reference to FIG. 7c.

In FIG. 7c there is shown at 1 a control pulse delivered by a reference clock or control sequencer, at 2 the corresponding control signal for the drive means 11, 12 constituted by the motor-gearbox unit of FIG. 7a, at 3 the corresponding timing diagram for an end of travel limit switch on the shaft of the previously described motor-gearbox unit, at 4 the corresponding active and passive phases of the electromagnetic clutch coupling device 8, 9 and, finally, at 5 the armed and calibrated impact positions denoted I and II, in conformity with FIG. 7b, of the percussion head 14, 15 and the lever arm 6. It will be understood that in the previously mentioned FIG. 7c the active position of the electromagnetic clutch coupling device 8, 9 makes it possible to displace into and/or maintain in the calibrated impact armed position the percussion head 14, 15 and the lever arm 6 whereas the passive position of the latter enables the movement to the calibrated impact position denoted II. Also, the return of the electromagnetic clutch coupling device 8, 9 to the active position, as seen in FIG. 7c, makes it possible to capture the combination constituted by the lever arm 6 and the percussion head 14, 15 so as to prevent, in accordance with the invention, any rebound after a given calibrated impact. The sequential triggering of each of the percussion members Mi naturally makes it possible to generate in succession a plurality of calibrated impacts. The calibrated impacts may advantageously be generated at different points Pi or a plurality of calibrated impacts may be generated at the same point in order to obtain a plurality of values in order to determine average values. According to a specific characteristic of the device in accordance with the invention, the duration of the passive phase of the electromagnetic clutch coupling device 8, 9 previously described may be adjustable so as to achieve by adjusting this duration calibrated impacts without any rebound. This duration is determined experimentally according to the modulus of elasticity of the material of the percussion head 14 and the hardness of the surfacing. To give a non-limiting example, the percussion head 14 may be constituted by a superpolyamide plastics material such as the materials marketed by the company ERTA under the trade name ERTALON. A plastics material will preferably be chosen with a modulus of elasticity between 90 000 and 170 000 N/cm$^2$. The percussion head 14 may advantageously comprise a spherical dome-shaped percussion surface, the latter having a radius of curvature in the order of 20 cm, for example.

A more detailed description of the sensor means Ci associated with the percussion means Mi will now be given with reference to FIG. 8. The aforementioned figure represents a cutaway view of one particularly advantageous embodiment of the sensor means Ci showing the internal arrangement of the latter.

Referring to this figure, the sensor means Ci comprise a box 16 forming a chassis for the sensor means. In operation the box 16 is rendered mechanically fast with the mobile support 3 or with a support 19 fastened to the latter, through the intermediary of first decoupling spring means 18. As shown in FIG. 8, the box 16 or chassis is, depending on its non-functional or functional status, respectively rendered fast or not with the support 19 or 3, through the intermediary of a system comprising an actuator 25, a piston rod 26 and a ring 28 which make it possible to move the box 16 into contact with the support 19 when the latter is not operational, or, on the contrary, the rod 26 being disengaged from the ring 28, to render the box 16 fast with the mobile support 3 (19) through the intermediary only of the first decoupling spring means 18 when the sensor means Ci in question are operational. The sensor means Ci shown in FIG. 8 further comprise a sensing head 20, 21, 22, 23 mechanically fastened to the box forming the chassis 16 through the intermediary of second decoupling spring means 24. As seen also in FIG. 8, the sensing head may advantageously comprise a support lever arm 22 pivotting in rotation about a fixed shaft denoted 220 relative to the chassis 16. The opposite end of the lever arm 22 is mechanically fastened to the chassis 16 through the intermediary of the second decoupling means 24. The sensing head further comprises a sensing cell 20, 21 mechanically fastened to the lever arm 22 through the intermediary of third decoupling spring means 23. In an advantageous embodiment the sensing cell 20, 21 may comprise an electromechanical transducer 20 of the accelerometer or geophone type. The sensitive surface of the transducer 20 is mechanically fastened to a spike 21 made from a hard material adapted to be placed in contact with the measurement point on the surface of the surfacing. Accelerometers thus constitute acceleration sensors with a frequency bandwidth substantially between 0 and 10 000 Hz. Geophones, on the other hand, constitute speed sensors with a bandwidth substantially between 4 Hz and 5 000 Hz. The spike 21 may itself be made from very hard steel and the force with which the spike bears on the surfacing may, to give a non-limiting example, be equal to 1 Newton in the case where the electromechanical transducer is an accelerometer with a mass of 2 grammes or 10 to 20 Newtons in the case where the electromechnical transducer is a geophone with a mass in the order of 20 g. The radius of curvature of the spike 21 may be in the order of a few millimeters.

Figure 8:
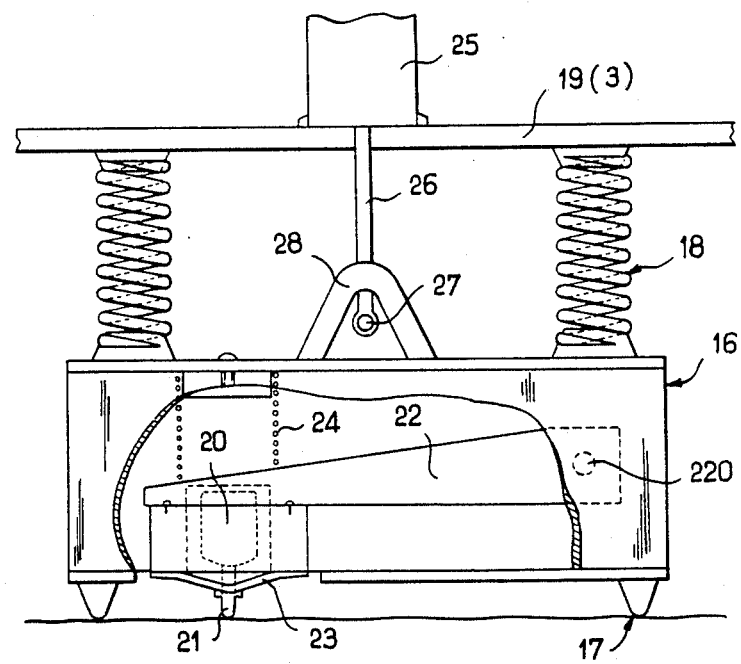

Thus, given the structure of each of the sensors Ci as shown in FIG. 8, the latter jointly serve to establish a force with which the spike 21 bears on the surfacing through the intermediary of the first, second and third decoupling spring means in particular with appropriate vibrational decoupling, the third decoupling means 23 having the effect in particular of mechanically decoupling the sensing cell 20, 21 and the lever arm 22 by increasing the bandwidth at high frequencies, the only mass as seen by the spike 21 at these frequencies being the mass of the spike plus that of the geophone but virtually none of that of the arm 22. In order to seat the box 16 forming the chassis on the surfacing under test during operation, it comprises as seen in FIG. 8 three support spikes 17 adapted to come into contact with the latter surface. Thus, given the inherent structure of each of the sensing means Ci shown in FIG. 8, and in particular given the presence of the first, second and third decoupling means previously described, the force with which the box 16 is applied to the surfacing through the intermediary of the spikes 17 is determined only by the first decoupling means 18 whereas the force with which the spike 21 is pressed into contact with the measurement point is determined only by the lever system 22, second decoupling means 24 and third decoupling means 23. Laboratory tests comparing a sensor directly stuck in the vicinity of a test point Pi and sensor means Ci as shown in FIG. 8 have shown a very high degree of similarity of the response characteristics.

Figure 9:
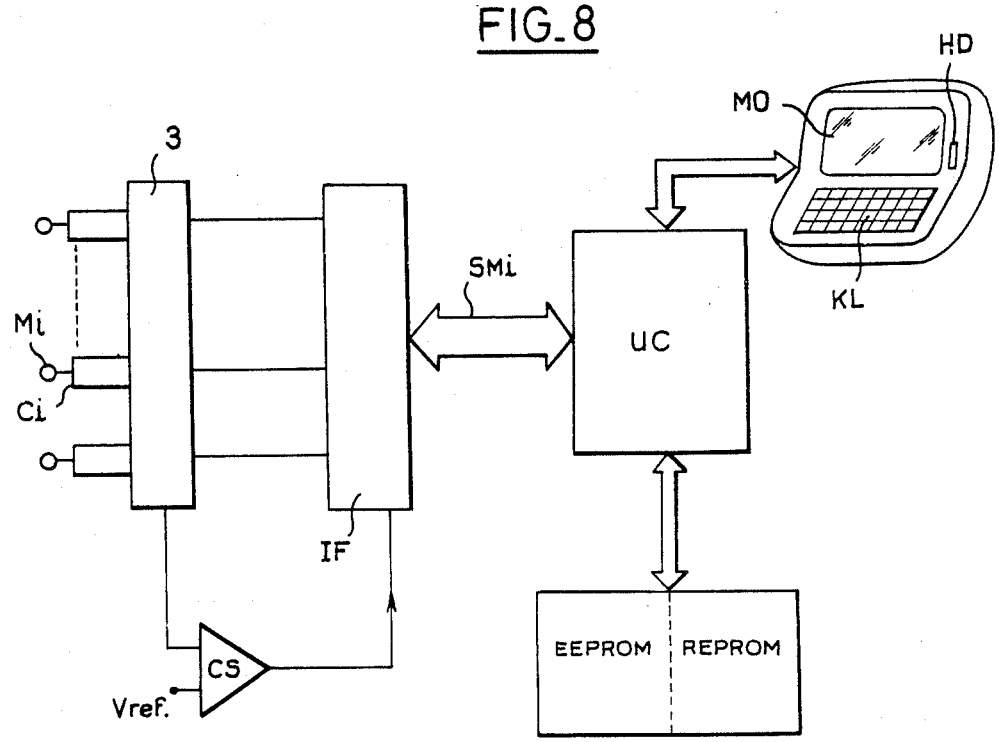

A more detailed description of the architecture of the device in accordance with the invention for mechanical testing of civil engineering structure surfacings from the point of view of its functional arrangement will now be given with reference to FIG. 9.

As seen in this figure, the device advantageously further comprises processor means for sequential control of the device and processor means for processing the reference and measurement signatures according to the method in accordance with the invention as previously described.

The control processor and calculation means advantageously comprise a microcomputer provided with peripheral deices. To give a non-limiting example, the peripheral devices may comprise a control keyboard denoted KL and a display monitor denoted MO. The microcomputer is symbolically represented by its central processor unit denoted UC. The peripheral devices of the microcomputer may further comprise non-volatile memory means used to memorise digital values representative of the measurement signatures. The aforementioned non-volatile memory means may comprise, for example, a magnetic hard disk HD, given the very large number of measurements to be carried out, given the large number of test points. The peripheral devices of the microcomputer may advantageously further comprise electrically reprogrammable (EEPROM) type memory means in which are memorised digital values representative of the so-called reference signatures. These, after they are established on a reference test area as previously described with reference to FIG. 1, may be memorised and, where necessary, modified because of specific experimental or utilisation circumstances. Finally, the peripheral devices of the microcomputer may comprise reprogammable read-only (REPROM) type memory means in which there is memorised a program for calculating and processing values in order to compare the signatures SMi with the reference signatures 2a through 2i to establish an identification on the basis of resemblance criteria as already described previously in this description.

Finally, the control processor means comprise control interfaces denoted IF, analogue-digital/digital-analogue input/output interfaces connected to the drive members and the control members of the percussion members Mi and the sensor means Ci. These control interfaces will not be described in that they may be constituted by any means available through normal commercial channels.

In an advantageous embodiment of the device in accordance with the invention for mechanical testing of civil engineering structure surfacings, the previously described input/output control interface means IF may advantageously comprise a sensor responsive to the peak value of the amplitude of the calibrated impact generated by a percussion means Mi. This peak value sensor delivers through the intermediary of a threshold circuit denoted CS, and relative to a specific reference voltage denoted Vref, a pulse for triggering the electromagnetic clutch coupling device 8, 9 so as to avoid successive rebounding of each percussion member Mi after the calibrated impact is applied. It will be understood, of course, that the sensor itself may be constituted by the sensor means Ci associated with the corresponding percussion means Mi, the signal delivered by each sensor Ci being compared with a reference value substantially corresponding to the peak value of the signal generated by the impact pulse. The pulse delivered by the threshold circuit CS then serves, through the intermediary of the interface IF, to control via the central processor unit UC the electromagnetic clutch coupling means in order to engage the latter, after a predetermined time-delay, in order to prevent any consequent rebound.

There has thus been described a method and a device for mechanical testing of civil engineering structure surfacings that offer particularly high performance. Use of the device as previously described, in particular with reference to the aforementioned FIGS. 6 through 9, may advantageously be effected sequentially by the operator. A phase for mechanical initialisation of the device being provided first of all, the plurality of sensor means Ci is first placed in position, the feet 17 of each of the latter being placed in contact with the ground by the operator. The control processor system previously described having been appropriately initialised, the mobile support 3 naturally being maintained stationary at the level of the spikes, the operator can then initiate the sequence of impulse impacts generated by each of the percussion means Mi in succession. The data or signatures corresponding to the test point Pi or Pij are then memorised in succession by the central processor unit UC and a first measurement sequence on a previously described alignment carried out; the operator can then move all of the device in the translation direction T, and in particular the mobile support 3, so as to position the system for a new sequence, and so on. The distance of such displacement may be determined by the operator to produce a meshed array as previously described.

The use of a device comprising three pairs of sensors Ci, percussion members Mi on a mobile support 3 has made it possible to test a motorway surfacing, the duration of the operation for one kilometer, representing approximately 200 cast concrete slabs, having been 2.15 hours. The device and the method in accordance with the invention have thus made it possible to test motorway surfacings over a distance of 2.77 km in a working day of 6 hours.

I claim:

1. Method for mechanical testing of civil engineering structure surfacing, characterised in that it comprises:
    establishing at least one signature (a) of the response of a reference sound surfacing to an impulse impact,
    establishing a plurality of signatures 2b–2i) of the response to a calibrated impulse impact of a surfacing of the same type in which reference sample defects have been formed, said signatures relating to the reference sound surfacing and to the surfacing comprising the sample defects constituting reference signatures,
    submitting a plurality of specific points (Pi) on said surfacing to be tested to at least one impulse impact in order to determine the signature (SMi) of the impulse response at each of said specific points (Pi),
    comparing the impulse response signatures of said points to reference measurement signatures (2a–2i) established by said calibrated impulse impacts to thereby establish an identification based on resemblance criteria.

2. Method according to claim 1, characterised in that said reference signatures (2a–2i) and said measurement signatures (SMi) are the responses to an impact pulse in a mobility-frequency diagram.

3. Method according to claim 1, characterised in that the impact pulses for establishing the reference and measurement signatures are calibrated impact pulses.

4. Method according to claim 1, characterised in that said measurement signatures are compared with said reference signatures by:
    comparing specific values of the mobility-frequency diagram of the measurement signatures to corresponding values, referred to hereinafter as inherent values, of the reference signatures (2a–2i),
    calculating a correlation or resemblance coefficient enabling the aforementioned identification to be obtained.

5. Method according to claim 1, characterised in that said specific points at which said surfacing is subjected to at least one impulse impact test are distributed in a meshed array (Pij), the increment (r) of the array being determined according to the resolution required.

6. Device for mechanical testing of civil engineering structure surfacings, characterised in that it comprises:
    a mobile support (3) adapted to be moved (T) across the surface of the surfacing,
    percussion means (Mi) disposed on the support (3), said means (Mi) serving to generate sequential calibrated test impacts on said surface of the surfacing,
    sensor means (Ci) fastened to the mobile support, said sensor means being mechanically decoupled from the support (3), said sensor means (Ci) serving to deliver an electrical signal representative of the impulse response of the surfacing to the calibrated test impacts.

7. Device according to claim 6, characterised in that the percussion means (Ci) are constituted by a plurality of percussion members aligned ($\delta$) on the mobile support (3), the resulting alignment being transverse to the direction of displacement (T) of the support.

8. Device according to claim 7, characterised in that with each percussion member (Mi) there is associated a sensor member (Ci), the set of receiver members constituting the sensing means.

9. Device according to claim 8, characterised in that the drive means (8, 9, 10) for the arm comprise:
    an electromagnetic clutch coupling device (8, 9) mechanically fastened to said arm (6) forming a lever arm,
    drive means (10, 11) for rotating said clutch, said rotational drive means (10, 11) and said clutch coupling device (9, 10) serving to displace the arm (6) forming a lever and the percussion head (14, 15) into a calibrated impact armed position,
    return spring means (13) mechanically fastened to the support (3) and to the arm (6) forming a lever arm, said return spring means (13) and said clutch coupling device (9, 10) serving to displace the arm (6) forming a lever arm and the percussion head (14, 15) to a calibrated impact position.

10. Device according to claim 7, characterised in that said calibrated impacts consist in an impact pulse with an amplitude between 100 and 1000 daN and with a duration less than or equal to 1 ms.

11. Device according to claim 6, characterised in that each percussion member (Mi) comprises:
    a percussion head (14, 15) mounted at the end of an arm (6) forming a lever arm and movable in rotation about an axis (7) substantially parallel to said alignment ($\delta$),
    drive means (8, 9, 10) for said arm (6) serving, through an intermediary of the percussion head (14, 15), to generate in succession a plurality of calibrated impacts.

12. Device according to claim 6, characterised in that the sensor means (Ci) comprise:
    a box (16) forming a sensor means chassis which, in operation, is rendered mechanically fast with the mobile support (3) through the intermediary of first decoupling spring means (18),
    a sensing head (20, 21, 22, 23) mechanically fastened to the box (16) forming the chassis through the intermediary of second decoupling spring means (24).

13. Device according to claim 12, characterised in that the sensing head comprises:
    a support lever arm (22) pivotted to rotate about an axis fixed relative to the chassis (16), the opposite end of the lever arm being mechanically fastened to the chassis (16) through the intermediary of said second decoupling spring means (24),
    a sensing cell (20, 21) mechanically fastened to the lever arm (22) through an intermediary of third decoupling spring means (23).

14. Device according to claim 13, characterised in that the sensing cell (20, 21) comprises:
    an electromechanical transducer (20) of the accelerometer or geophone type, the sensitive surface of said transducer being mechanically fastened to a hard material spike (21) adapted to be placed in contact with the measurement point on the surface of the surfacing.

15. Device according to claim 12, characterised in that the box (16) forming the chassis comprises three support spikes (17) adapted to come into contact with the surfacing.

16. Device according to claim 6, characterised in that it further comprises device sequential control processing means and reference and measurement signature processing calculation means.

17. Device according to claim 16, characterised in that said control processing and calculation means comprise:
a microcomputer provided with peripheral devices, said peripheral devices including:
non-volatile memory means serving to memorise digital values representative of said measurement signatures,
electrically reprogrammable memory (EEPROM) type memory means in which are memorised digital values representative of the so-called reference signatures,
reprogrammable read only memory (REPROM) type memory means in which is memorised a program for computing and processing values to compare the measurement signatures (SMi) with the reference signatures ($2a-2i$) in order to establish an identification based on criteria of resemblance,
input/output control (analogue-digital/digital-analogue) interfaces connected to the drive and control means for the percussion members (Mi) and the sensing means (Ci).

18. Device according to claim 17, characterised in that said input/output control interfaces include a sensor responsive to the peak value of the calibrated impact amplitude, said sensor delivering through the intermediary of a threshold circuit a pulse to trigger the electromechanical clutch coupling device to prevent rebounding of each percussion member (Mi) after application of a calibrated impact.

* * * * *